United States Patent
Jain et al.

(10) Patent No.: US 6,629,968 B1
(45) Date of Patent: *Oct. 7, 2003

(54) SHELF STORAGE STABLE IONTOPHORESIS RESERVOIR-ELECTRODE AND IONTOPHORETIC SYSTEM INCORPORATING THE RESERVOIR-ELECTRODE

(75) Inventors: Uday K. Jain, Mahway, NJ (US); Vilambi N R K Reddy, Trichy TamiNadu (IN); Bruce M. Eliash, Franklin Lakes, NJ (US); Kevin John Carey, North Plainfield, NJ (US); Vitaly Falevich, Ozone Park, NY (US); Preston Keusch, Hazlet, NJ (US)

(73) Assignee: Vyteris, Inc., Fair Lawn, NJ (US)

( * ) Notice: Subject to any disclaimer, the term of this patent is extended or adjusted under 35 U.S.C. 154(b) by 163 days.

This patent is subject to a terminal disclaimer.

(21) Appl. No.: 09/610,563

(22) Filed: Jun. 30, 2000

(51) Int. Cl.[7] .................. A61M 31/00; A61N 00/30
(52) U.S. Cl. ................ 604/501; 604/20; 424/449
(58) Field of Search .................. 604/20, 890.1, 604/49, 501; 607/149, 115, 152–153, 62; 424/449, 448, 78.12; 514/772

(56) References Cited

U.S. PATENT DOCUMENTS

| 4,416,274 A | 11/1983 | Jacobsen et al. | |
| 4,474,570 A | * 10/1984 | Ariura et al. | 604/20 |

(List continued on next page.)

FOREIGN PATENT DOCUMENTS

| WO | WO 98/20869 | 5/1998 |
| WO | WO 01/91848 | 12/2001 |

OTHER PUBLICATIONS

U.S. patent application Ser. No. 09/584,453,Bernhard et al., filed May 31, 2000.

*Primary Examiner*—Henry Bennett
*Assistant Examiner*—Kathryn Ferko
(74) *Attorney, Agent, or Firm*—Kirkpatrick & Lockhart LLP

(57) ABSTRACT

A reservoir-electrode for an iontophoretic delivery device of the present invention includes an electrode; and a hydrophilic reservoir situated in electrically conductive relation to the electrode. The reservoir is formed from a bibulous hydrophilic cross-linked polymeric material having a substantially uniform concentration of an alkali metal chloride salt therein thereby substantially eliminating concentration gradients of the salt with respect to the electrode. The polymeric material has a first surface and a second surface that is adhesively adherent to the electrode. The first surface of the polymeric material is releasably adhesive to an applied area of a patient's skin. The polymeric material has a cohesive strength, wherein a bond strength of an adhesive bond between the second surface of the polymeric material to the electrode is greater than the cohesive strength of the polymeric material and an adhesive bond strength of the first surface of the polymeric material to the applied area of the patient is less than the cohesive strength of the polymeric material so that upon removal of the reservoir-electrode from the applied area of the patient, substantially no polymeric material remains on the applied area and the reservoir remains substantially intact and adhesively adherent to the electrode.

13 Claims, 4 Drawing Sheets

U.S. PATENT DOCUMENTS

| | | | | |
|---|---|---|---|---|
| 4,752,285 A | | 6/1988 | Petelenz et al. | |
| 4,764,164 A | * | 8/1988 | Sasaki | 604/20 |
| 5,084,008 A | * | 1/1992 | Phipps | 75/10.1 |
| 5,135,477 A | | 8/1992 | Untereker et al. | |
| 5,203,768 A | * | 4/1993 | Haak et al. | 604/20 |
| 5,320,598 A | | 6/1994 | Haak et al. | |
| 5,354,790 A | * | 10/1994 | Keusch et al. | 252/500 |
| 5,362,308 A | * | 11/1994 | Chien et al. | 604/20 |
| 5,374,241 A | | 12/1994 | Lloyd et al. | |
| 5,385,543 A | | 1/1995 | Haak et al. | |
| 5,405,317 A | * | 4/1995 | Myers et al. | 604/20 |
| 5,415,628 A | | 5/1995 | Untereker et al. | |
| 5,443,442 A | * | 8/1995 | Phipps et al. | 604/20 |
| 5,464,387 A | * | 11/1995 | Haak et al. | 604/20 |
| 5,543,098 A | * | 8/1996 | Myers et al. | 264/104 |
| 5,582,587 A | * | 12/1996 | Gyory et al. | 604/20 |
| 5,618,265 A | * | 4/1997 | Myers et al. | 604/20 |
| 5,647,844 A | * | 7/1997 | Haak et al. | 424/449 |
| 5,766,144 A | * | 6/1998 | Lai et al. | 604/20 |
| 5,817,044 A | | 10/1998 | Evers et al. | |
| 5,837,281 A | * | 11/1998 | Iga et al. | 424/449 |
| 5,882,677 A | * | 3/1999 | Kupperblatt | 424/405 |
| 5,908,400 A | * | 6/1999 | Higo et al. | 604/20 |
| 5,983,130 A | * | 11/1999 | Phipps et al. | 604/20 |
| 5,990,179 A | * | 11/1999 | Gyory et al. | 514/329 |
| 6,004,577 A | * | 12/1999 | Murdock | 424/400 |
| 6,049,733 A | * | 4/2000 | Phipps et al. | 424/449 |
| 6,064,908 A | * | 5/2000 | Muller et al. | 604/20 |
| 6,071,508 A | * | 6/2000 | Murdock | 424/449 |
| 6,295,469 B1 | * | 9/2001 | Linkwitz et al. | 604/20 |
| 6,350,259 B1 | * | 2/2002 | Sage et al. | 604/501 |
| 6,496,727 B1 | * | 12/2002 | Bernhard et al. | 604/20 |

\* cited by examiner

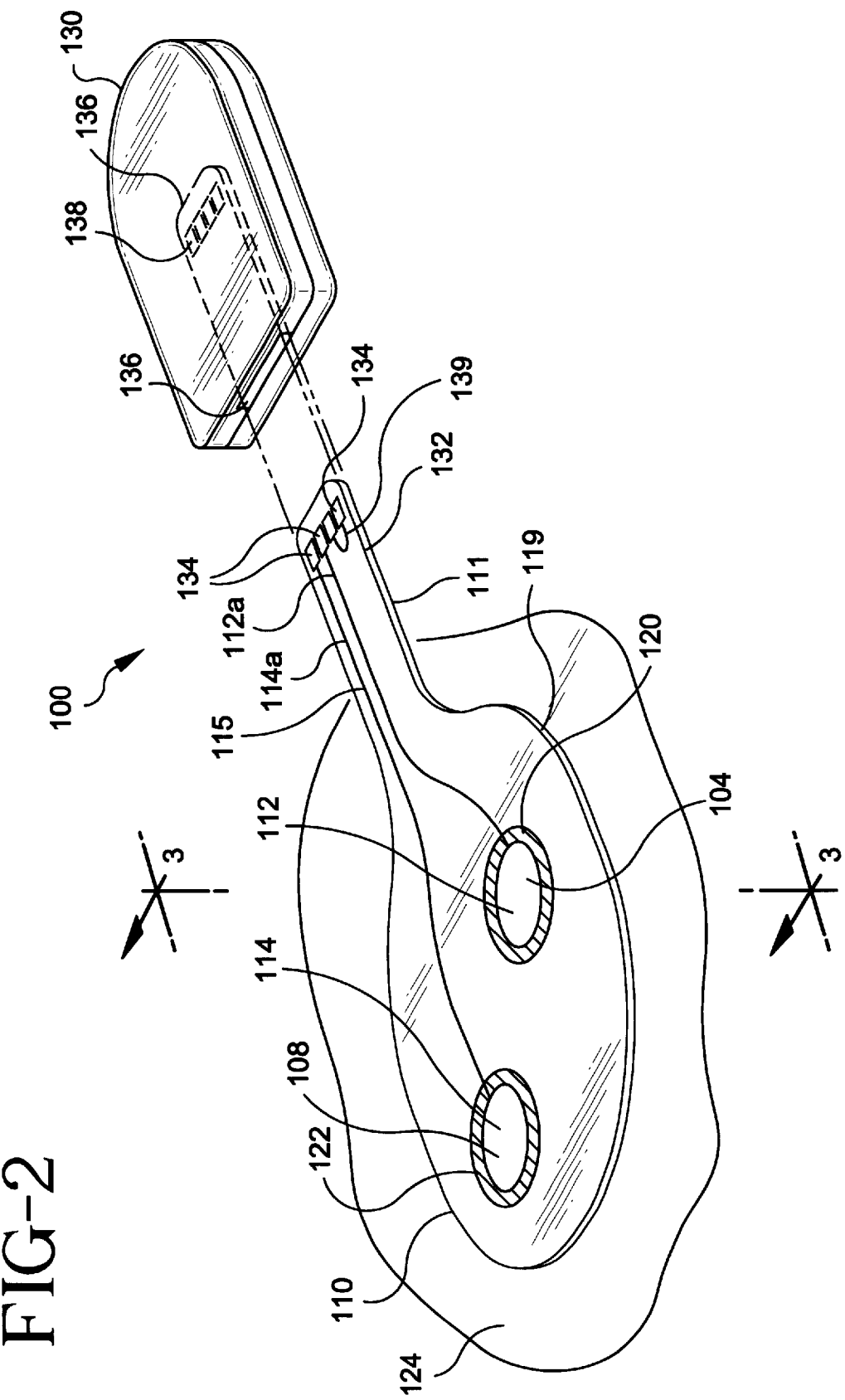

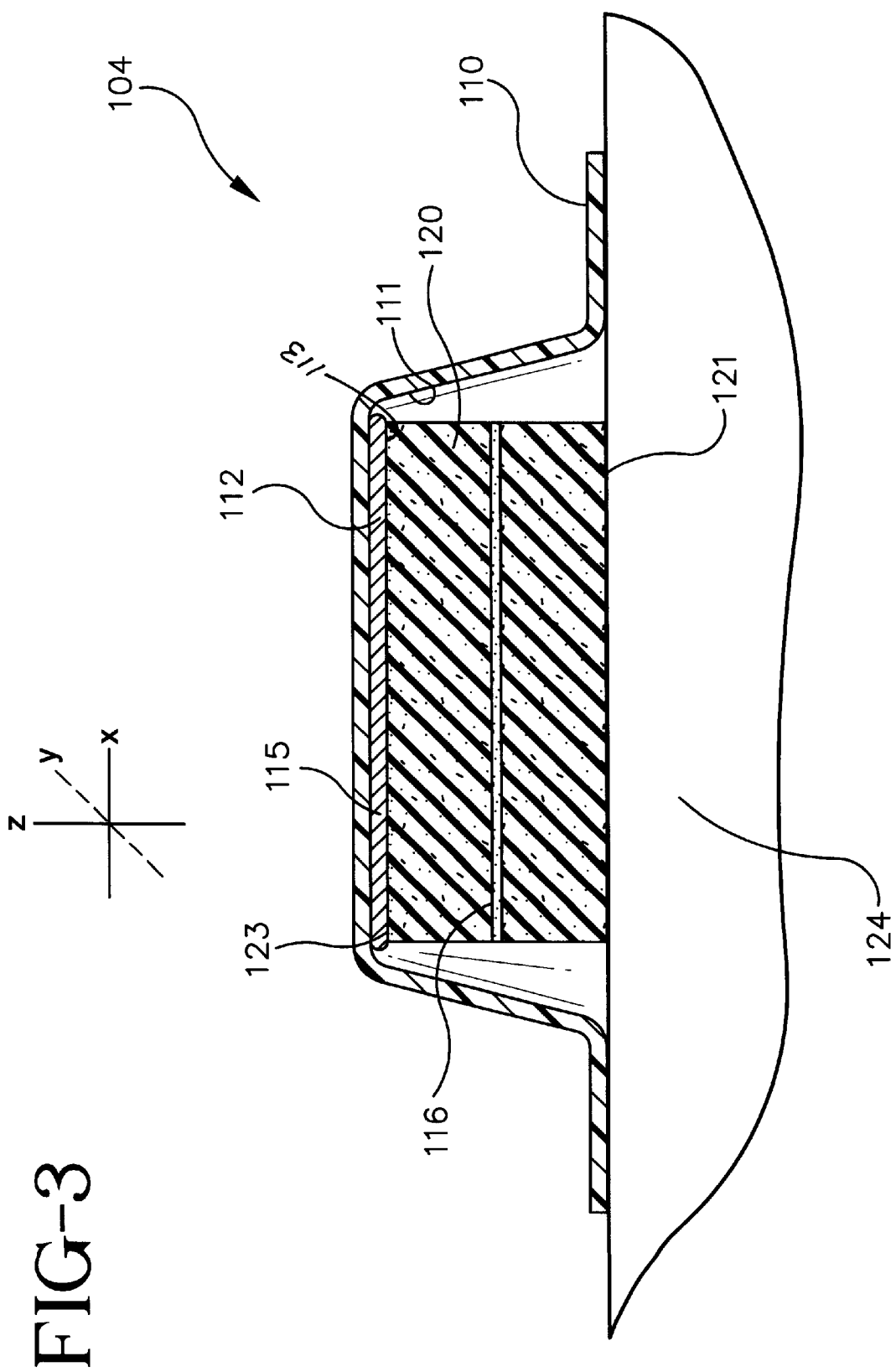

SHELF STORAGE STABLE IONTOPHORESIS RESERVOIR-ELECTRODE AND IONTOPHORETIC SYSTEM INCORPORATING THE RESERVOIR-ELECTRODE

FIELD OF THE INVENTION

The present invention is generally related to transdermal drug delivery and more particularly to a reservoir-electrode for iontophoresis that has enhanced stability properties.

BACKGROUND

Iontophoretic delivery of a medicament is accomplished by application of a voltage to a medicament loaded reservoir-electrode, sufficient to maintain a current between the medicament loaded reservoir-electrode and a return electrode (another electrode) applied to a patient's skin so that an ionic form of the desired medicament is delivered to the patient.

Shelf storage stability problems for many of the iontophoresis devices reported in the literature require that the medicament be stored separately from the reservoir-electrode until immediately prior to use. Iontophoretic delivery of medicaments is recognized as desirable for many medicaments, but it is not widely used because no devices are commercially available that meet all of the needs of the potential user population. An important requirement for a product to enjoy widespread usage is shelf storage stability. In an iontophoretic drug delivery system, one needs to be concerned not only with the drug stability, but also the stability of the delivery device and any interaction between the several components.

If a drug product is not stable under normal shelf storage conditions, it is unlikely to be a successfully commercial product because the short shelf life limits the products utility to most potential users as most of the product's useful life is exhausted during the time required for manufacturing and the distribution process. Thus, determination of shelf storage stability is an important part of a drug product's regulatory approval process. If there are difficulties with storage stability, regulatory approval may be withheld. Often, in iontophoretic devices the reservoir-electrode also is maintained in a dry (unhydrated) condition prior to use also because of the tendency of the active electrode material to undergo physical and chemical changes during shelf storage. Many drugs are not particularly stable to ambient conditions as the free base compound and as a result are formulated as salts that may react unfavorably with electrodes in iontophoretic devices. The need to store the several components separately has limited the use of iontophoretic devices, since in order to use the device, the reservoir-electrode needs to be charged with the medicament and hydrated either by a practitioner or user immediately prior to use.

Several United States Patents disclose devices that attempt to overcome the problem of shelf storage stability and facilitate the preparation of the device for use. U.S. Pat. No. 5,320,598 discloses a dry-state iontophoretic drug delivery device that has drug and electrolyte reservoirs that are initially in a non-hydrated condition. The device has a liquid containing pouch or breakable capsules that contain water or other liquid, the liquid being releasable by disrupting the liquid containers prior to use. Commercial manufacture of a device utilizing this disclosure would be complex.

U.S. Pat. No 5,385,543 also discloses a dry-state iontophoretic drug delivery device that has drug and electrolyte reservoirs. The disclosed device includes a backing layer with at least one passageway therethrough that allows the introduction of water or other liquids into the drug and electrolyte reservoirs prior to use followed by joining the reservoirs to the electrodes. The patent teaches that by joining the reservoirs to the electrodes after hydration, delamination problems are reduced.

No commercial products utilizing the technology disclosed either in the '598 or the '543 patents have been produced.

A different approach to the shelf storage stability problem is disclosed in U.S. Pat. No. 5,817,044. In this disclosure, the device is divided or otherwise separated into at least two portions, with one portion containing the electrode reservoir and the other containing the drug reservoir, which may include a medication in a dry form. In this disclosure, the user causes the two portions to come into electrical conducting contact with one another to at least partially hydrate one of the reservoirs, by either folding the device to bring the two portions into contact with one another or by removing a barrier dividing the two portions. While this device seems to be somewhat easier to use than the devices disclosed in the above patents, there currently is no commercial device that utilizes this disclosure.

International Application WO 98/208869 discloses an iontophoretic device for delivery of epinephrine and lidocaine HCl. The disclosed device includes materials that deter microbial growth and anti-oxidants to enhance the stability of epinephrine. While this disclosure recognizes the need for shelf storage stability and addresses the problem of epinephrine stability by including anti-oxidants, there is no recognition of the need to prevent corrosion of the electrodes during manufacture and shelf storage. Again, there is no commercial product based on the information in this disclosure.

A commercial iontophoretic device for delivery of lidocaine and epinephrine is provided under the tradename "Numby Stuff" by the Iomed Corp., Salt Lake City, Utah. The "Numby Stuff" device kit includes a vial sealed with a rubber septum containing a trademarked "Iontocaine" solution that includes Lidocaine HCl 2% and Epinephrine 1:100,000 that is used for charging the "Phoresor" system immediately prior to use. The "Numby Stuff" device lists U.S. Pat. Nos. 4,752,285; 5,374,241; 4,416,274; 5,135,477; and 5,415,628 that describe aspects of the device. None of these patents disclose a medicament-charged iontophoretic device with a useful shelf life. The patents are directed toward aspects of the delivery process and reservoir-electrode design. While these disclosures do potentially address the problem of keeping the medicament stable by isolating it from moisture, oxidation or from other components of the device, there is the problem, not previously recognized in the literature, corrosion of the active electrode during manufacture and storage. This problem is best understood by considering an electrochemical cell consisting of the silver/silver chloride electrode system commonly used in iontophoretic devices. In the cell considered, the Ag/AgCl electrode can be surround by solution of different chloride ion concentrations ($Cl_1$ and $Cl_2$. The electrode reaction is illustrated by $$Ag + Cl^- = AgCl + e^-.$$

The Nernst equation describing this cell is

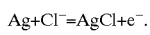

The Nernst equation illustrates that a chloride concentration gradient ($[Cl_1]$ not equal to $[Cl_2]$) results in an open circuit potential, commonly called a concentration potential, that results in corrosion.

$\Delta E_0$=open circuit potential as the concentration of Cl⁻ moves away from unit concentration or activity.

Based on the Nernst equation's dependency on the log of the chloride ion concentration, the effect on the open circuit potential is about 60 millivolts (mV) per decade ($10^1$) in concentration of chloride ion. Silver/silver chloride electrodes are the most common iontophoretic electrodes, and these electrodes require chloride ion to function. Most iontophoretic medicaments are provided as the hydrochloride salt and are added to the reservoir at some point prior to use. The practical effect of this phenomenon is, since the log of zero is infinity, that when chloride ion is added to the device before use, before the concentration of chloride ion can fully equilibrate, there is likely already some corrosive damage to the patch due to concentration differentials. Thus, there is often some corrosive damage to the reservoir-electrode interface almost immediately upon the addition of chloride ion containing constituents to the reservoir. Additionally, if the chloride ion addition is non-uniform, some corrosive conversion of silver to silver chloride is almost guaranteed to occur. Several problems can arise from this corrosion to the electrode including: a loss of pharmaceutical elegance; a cut-off of the operation of the reservoir-electrode because of an open circuit; localized pH changes in the reservoir-electrode during operation; a reduction in the amount of silver available to the desired electrochemical reaction during iontophoresis; and actual delivery of silver ion to the patient resulting in a "tattoo". One way to deal with this chloride concentration gradient problem is to use sufficient excess amounts of silver so that the reservoir-electrode is still substantially functional despite some corrosion. Often, even if excess silver is used, localized corrosion can produce in a break in the electrode continuity at a junction point and result in, at least, a partially non-functional reservoir-electrode. A further safety related problem may occur if a portion of the reservoir electrode is non-functional. When a portion of the reservoir electrode is non-functional, the full current of the controller is applied to a smaller area of the reservoir-electrode resulting in an undesirably high current density. The higher current density may cause undesirable effects to the patient ranging from a "tingling" sensation from the increased current to damage to the skin contact area. Additionally, since silver is a "precious" metal, the use of excess silver also adversely effects the cost, and ultimately, the possible commercialization of iontophoretic drug delivery.

Another way to minimize the effect of the rapid onset of corrosion due to a chloride ion concentration gradient is to form the reservoir electrode from a very absorbent material, so that the hydration process occurs rapidly, minimizing the duration of any concentration gradient. While a very absorbent reservoir reduces the problem of corrosion when loading, such an absorbent material generally readily expresses liquid upon compression and, additionally, does not have any self-adhesive properties that helps the adherence of the reservoir material to the electrode or to the patient's skin.

Most commonly, an iontophoretic reservoir is formed from a hydrogel. Hydrogels are absorbent and generally do not express liquid upon compression, but a medicament may be slow to absorb into the hydrogel, and as a result, the slow rate of absorption amplifies the problem of concentration gradient induced corrosion before equilibrium concentration is achieved. Currently, the only way a hydrogel reservoir may be incorporated into an iontophoretic reservoir-electrode is to charge the hydrogel reservoir with the desired aliquot of medicament independently of the electrode, allow the medicament solution to equilibrate within the hydrogel, a process which can easily require several days and then laminate the loaded hydrogel to the electrode to form the reservoir-electrode. The separate hydrogel loading process is not amenable to continuous high-speed manufacturing and adversely effects the potential for commercialization of hydrogel based reservoir-electrodes.

If a reservoir-electrode were available that addressed the problem of corrosion between the electron conductor and the ion conductor interface due to electrolyte concentration imbalances so that the device could be preloaded with medicament and still have acceptable shelf storage stability, the practicability of iontophoretic drug delivery would be enhanced. If such a reservoir-electrode also had sufficient adhesive properties to enhance adherence of the reservoir material to the electrode and to the patient's skin, the art of iontophoresis would be further enhanced. Such a reservoir-electrode is disclosed hereinbelow.

SUMMARY

A reservoir-electrode for an iontophoretic delivery device of the present invention includes an electrode having a surface; and a hydrophilic reservoir situated in electrically conductive relation to the electrode. The reservoir is formed from an absorbent material having a substantially uniform concentration of an alkali metal salt therein thereby substantially eliminating concentration gradients of the salt with respect to the electrode surface so that when an aliquot of a medicament solution including ions of the salt is added to the reservoir substantially no corrosion potential develops at the surface of the electrode, thereby substantially eliminating a corrosive effect on the electrode.

An iontophoretic system of the present invention includes a first-reservoir electrode including at least one medicament for delivery to a patient. The first reservoir-electrode includes a first hydrophilic reservoir situated in electrically conductive relation to a first electrode with a surface. The first reservoir is formed from a bibulous hydrophilic cross-linked polymeric material having a substantially uniform concentration of an alkali metal chloride salt therein thereby substantially eliminating concentration gradients of the salt with respect to the electrode surface when an aliquot of at least one medicament including ions of the alkali metal chloride salt is added to the reservoir electrode. The polymeric material has a first surface and a second surface that is adhesively adherent to the electrode. The first surface of the polymeric material is releasably adhesive to an applied area of a patient's skin. The polymeric material has a cohesive strength, wherein a bond strength of an adhesive bond between the second surface of said polymeric material to the first electrode is greater than the cohesive strength of said polymeric material and an adhesive bond strength of the first surface of the polymeric material to the applied area of the patient is less than the cohesive strength of said polymeric material so that upon removal of the first reservoir-electrode from the applied area of the patient, substantially no polymeric material remains on the applied the said first electrode.

The iontophoretic system of the invention also includes a second reservoir-electrode including a second hydrophilic reservoir situated in electrically conductive relation to a second electrode with a surface. The second reservoir is formed from a bibulous hydrophilic cross-linked polymeric material having a substantially uniform concentration of an alkali metal chloride salt therein thereby substantially eliminating concentration gradients of the salt with respect to the second electrode. The polymeric material has a first surface and a second surface is adhesively adherent to the second electrode. The first surface of the polymeric material is releasably adhesive to an applied area of a patient's skin. The polymeric material has a cohesive strength, wherein a bond strength of an adhesive bond between the second surface of the polymeric material to the second electrode is greater than the cohesive strength of said polymeric material and an adhesive bond strength of the first surface of the polymeric material to the applied area of the patient is less than the cohesive strength of the polymeric material so that upon removal of the second reservoir-electrode from the applied area of the patient, substantially no polymeric material remains on the applied area and the second reservoir remains substantially intact and adhesively adherent to said second electrode. The iontophoretic system of the invention further includes a power supply disposed in electrically conductive contact with the first reservoir-electrode and the second reservoir-electrode to supply a preselected current so that when the first reservoir-electrode and the second reservoir-electrode are each applied to a patient, a complete electrical circuit is formed with the first reservoir-electrode operating as an anode and the second reservoir-electrode operating as a cathode, thereby delivering the at least one medicament to the patient.

The reservoir-electrode of the invention and the iontophoretic device incorporating reservoir-electrodes of the invention as both the active and the return reservoir-electrodes have demonstrated satisfactory shelf storage stability. The reservoir-electrode of the invention can be efficiently produced and, with the satisfactory shelf storage stability provided by overcoming the problem of electrode corrosion during storage, provides the opportunity for a previously unavailable commercial iontophoretic device that answers the both the needs of patients and commercial distribution requirements.

BRIEF DESCRIPTION OF THE DRAWINGS

FIG. 2 is a perspective view of an iontophoretic device of the invention incorporating an active reservoir-electrode and a return reservoir-electrode of the invention;

FIG. 3 is a cross-sectional view of a reservoir-electrode of the invention, taken from FIG. 2 along the line 3—3;

FIG. 4b is a schematic bottom plan view, analogous to FIG. 4a, of the reservoir-electrode of the invention after an identical period of shelf storage to the control of FIG. 4a.

DETAILED DESCRIPTION

Figure 1:
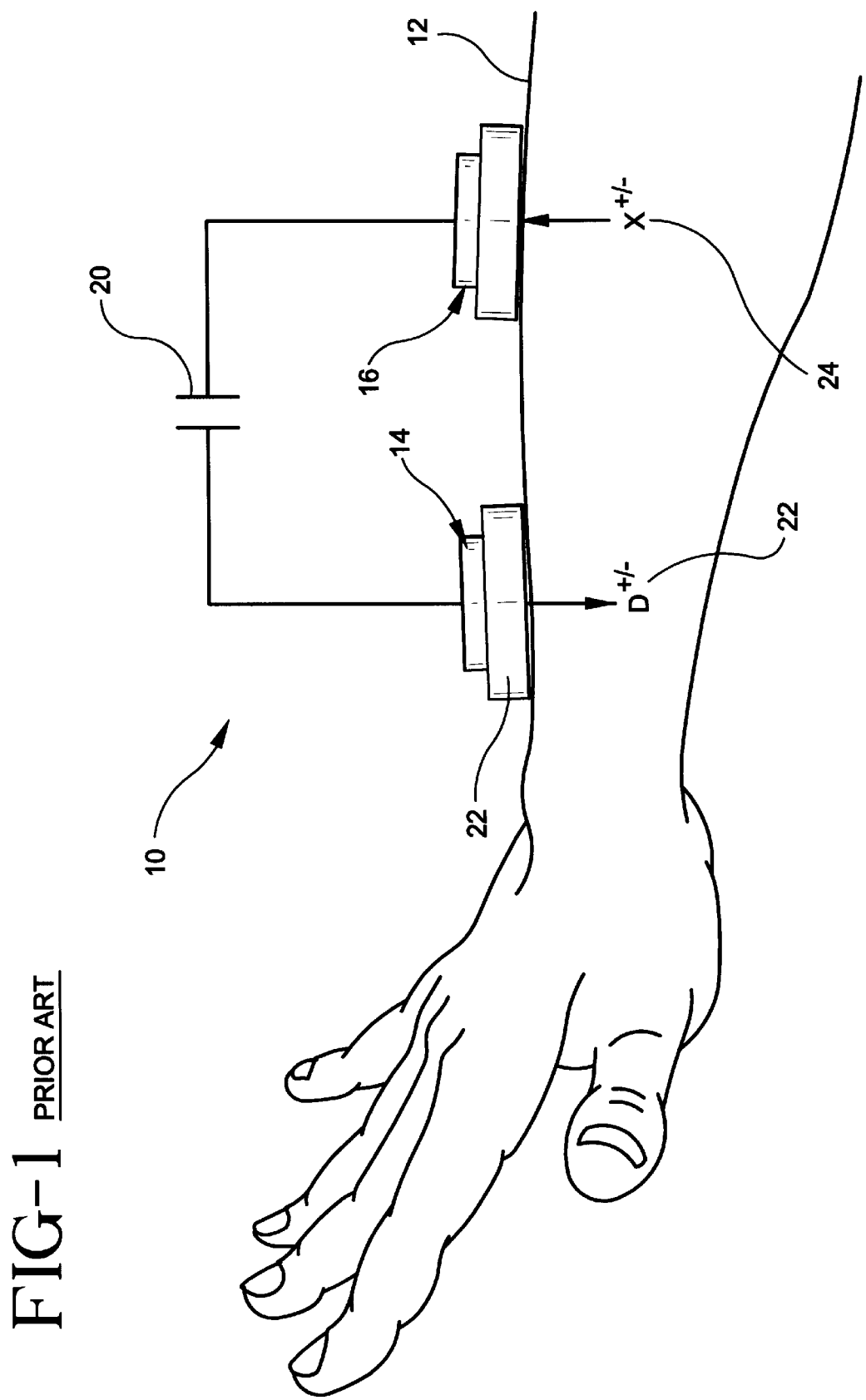
FIG. 1 (prior art) is a schematic view of an iontophoretic device positioned on a patient.

While this invention is satisfied by embodiments in many different forms, there are shown in the drawings and herein described in detail, embodiments of the invention with the understanding that the present disclosure to be considered as exemplary of the principles of the present invention and is not intended to limit the scope of the invention to the embodiments illustrated. The scope of the invention is measured by the appended claims and the equivalents.

Referring to FIG. 1, a generalized schematic iontophoretic device 10 is illustrated mounted on an applied area 12 of the arm of a patient. When iontophoretic device 10 is applied to skin 12 of a patient a completed circuit is formed between an anode 14 and a cathode 16 of device 10 and the patient. Iontophoretic device 10 includes a power supply 20 and a supply 22 of an ionized medicament to be delivered to the patient. When power supply 10 is activated and causes a current to flow between the electrodes, the ionized medicament is delivered into the patient and another ion 24 is removed from the patient. Generally, ionized medicaments are positively charged (cations). Thus, the active electrode is generally anode 14. In the instance where the medicament being delivered is an anion, cathode 16 is the active electrode and anode 14 is the return electrode.

A complete preferred prototype commercial iontophoretic device 100 is illustrated in FIGS. 2 and 3. Preferred Device 100 includes a first reservoir-electrode 104 (anode) charged with lidocaine HCl and epinephrine bitartrate and a second reservoir-electrode 108 intended to function as a cathode or return electrode as illustrated in FIG. 2. Device 100 includes a flexible backing 110 with first reservoir-electrode 104 and second reservoir-electrode 108 mounted thereon. Device 100 includes two electrodes 112 and 114, each having an electrode surface 113 and electrode interconnects 112a and 114a. Electrodes 112, 114 and electrode interconnects 112a and 114a are formed as a thin film deposited as traces onto flexible backing 110 with an inside surface 111. Preferably, electrodes 112 and 114 and electrode interconnects 112a and 114a are formed from conductive ink 115 applied as a thin film to inside surface 111. Conductive ink 115 preferably includes silver and silver chloride in a suitable binder material. Electrodes 112 and 114 each mounted with a preferred bibulous reservoirs, 120 and 122 respectively, formed from a cross-linked polymeric material such as cross-linked poly(vinylpyrolidone) hydrogel that each include a substantially uniform concentration of an alkali metal salt, preferably sodium chloride. The selection of the lidocaine HCl and epinephrine bitartrate used in this prototype are considered exemplary for the purpose of this disclosure and not limitative of the instant invention of a reservoir-electrode with the substantially uniform concentration of the alkali metal salt to eliminate concentration gradients that cause corrosion of the electrode. The Inventors believe that there is general applicability of the uniform concentration of the alkali metal salt as a corrosion preventative to substantially all reservoir-electrode material combinations and to other medicaments than those cited as examples in this disclosure.

The cross-linked poly(vinylpyrolidone) preferably includes a reinforcement 116, preferably a low basis weight non-woven scrim to provide shape retention to the hydrogel. The preferred reservoirs 120, 122 each have adhesive and cohesive properties that provide for a first surface 121, and a second surface 123. First surface 121 is preferably releasably adherent to an applied area 124 of a patient's skin. Second surface 123 is adhesively adherent to electrodes 112 and 114. In the device 100 of the invention, it is preferred that a bond strength of an adhesive bond formed between first surface 121 and applied area 124 of the patient's skin is less than the strength of an adhesive bond formed between second surface 123 and electrodes 112 and 114. Further, it is preferred that the strength of the releasable adhesive bond formed between first surface 121 and the patient's skin is less than the cohesive strength of the preferred reservoirs 120 and 122. These preferred adhesive and cohesive properties of reservoirs 120, 122 have the effect that when reservoir-electrodes 104, 108 of device 100 are removed from applied area 124 of the patient's skin, the reservoirs substantially cleanly come off patient's skin 124, leaving substantially no residue, stay substantially intact and do not come off of electrodes 112, 114 or backing 110.

Preferred device 100 also includes a power supply 130 that preferably supplies a preselected current or currents to the device when reservoir electrodes 104 and 108 are mounted on the patient's skin to form a completed circuit. Preferably, backing 110 includes an extended portion 132 with electrode interconnects 112a and 114a formed from conductive ink 115 extended thereon to connectors 134. Power supply 130 preferably includes a receptacle 136 with mating connectors 138 to receive extended portion 132 and connectors 134. Extended portion 132 with connectors 134 allows power supply 130 to be refitted with fresh backings 110 having reservoir-electrodes 104 and 108 thereon. Power supply 130 and backing 110 preferably includes a circuit 139 to identify the particular type of reservoir-electrodes and medicament to power supply 130.

In FIG. 3, a cross-sectional view of one reservoir-electrode of device 100 is shown. In this view, reservoir-electrode 104 includes electrode 112 and an absorbent reservoir 120 having a substantially uniform concentration of an alkali metal salt situated in electrically conductive relation to electrode 112 at electrode surface 113. Preferably, absorbent reservoir 120 is formed from a hydrophilic material, such as a bibulous hydrophilic cross-linked polymeric material, that has an alkali metal salt, preferably sodium chloride or other physiologically acceptable alkali metal salt. Preferably, bibulous hydrophilic cross-linked polymeric material of reservoir 120 has a first surface 121 and a second surface 123 that is adhesively adherent to electrode 112. Preferably, first surface 121 of reservoir 120 is releasably adhesively adherent when applied to an area 124 of a patient's skin. Preferred 120 has a cohesive strength and forms an adhesive bond with a bond strength between second surface 123 of the polymeric material to electrode 112 that is greater than the cohesive strength of the polymeric material. Additionally, an adhesive bond strength of first surface 121 of preferred polymeric reservoir 120 material to applied area 124 of the patient is less than the cohesive strength of polymeric reservoir 120 so that upon removal of reservoir-electrode 104 of the invention from applied area 124 of the patient, substantially no preferred polymeric reservoir 120 material remains on applied area 124 of the patient's skin and hydrophilic reservoir 120 remains substantially intact and adhesively adherent to electrode 112.

The preferred material for forming hydrophilic reservoir 120 is a cross-linked poly(vinylpyrolidone). The preferred material is prepared as a viscous aqueous syrup that incorporates the selected alkali halide, preferably sodium chloride, in the desired concentration. In the preferred embodiment of the invention, where the medicament to be delivered is lidocaine as the hydrochloride and epinephrine as the bitartrate, the active reservoir-electrode, i.e., containing the lidocaine and the epinephrine, is the anode because the medicaments being delivered are positive ions, the concentration of the sodium chloride is between about 0.001 to about one percent by weight (w/w). Preferably, in this application, the concentration is about 0.06 percent (w/w). For other applications, other concentrations and other pharmaceutically acceptable alkali metal salts may be preferred, and are considered within the scope of the invention. Additionally, in the case of the return reservoir-electrode 108 for the preferred embodiment of the invention, the same poly(vinylpyrolidone) is used. For the cathode application 108, the concentration of the alkali metal salt, again preferably sodium chloride, may be between about 0.001 percent to about one percent (w/w), with about 0.06 percent being preferred.

A preferred material for forming hydrophilic reservoir 120 is poly(vinylpyrolidone) (PVP) with a number average molecular weight greater than about 360,000 daltons. A suitable PVP is available from BASF, N.J. as PVP K-90F. When this material is prepared as a concentrated aqueous solution it forms a viscous syrup which is preferably applied to both sides of the reinforcement 116, placed between two release webs to a thickness of about of about 40 mils and subjected to conditions, preferably ionizing radiation, sufficient to cross-link the PVP sufficiently to substantially be shape retaining, flexible and having a preferred degree of tack. A preferred ionizing radiation is an electron beam having at least about a 1 MeV to deliver between about 1.0 and 2.5 megarads. Other sources of ionizing radiation such as $^{60}$Co or $^{137}$Cs may be used for particular applications. The degree of cross-link has considerable effect on the degree of tack. A low degree of cross-link results in high tack values, while a high degree of cross-link results in a low degree of tack. If there is insufficient cross-linking, resultant PVP reservoir 120 does not retain shape, may detach from reinforcement 116 and is extremely difficult to handle. If the degree of cross-linking is too great, the resultant PVP reservoir 120 has insufficient tack to adhere to electrode 112 or to patient contact area 124. Additionally, the degree of cross-link is preferably optimized so that the degree of swelling is controlled.

The use of the electron beam for cross-linking the PVP for reservoir 120 has a particular benefit to the present invention. Unlike gamma radiation that has a potential penetration of several feet of concrete, the electron beam penetration depth is described in the units of cm of water. This property of the electron beam can be utilized in controlling the degree of cross-link in reservoir 120. The exposure can be controlled so that there is a differential degree of tack on surface 121 than on surface 123 of reservoir 120. The differential degree of tack on the first surface and the second surface may be preselected to allow a sufficient degree of tack on surface 120 to ensure a sufficiently strong bond between electrode 112 and reservoir 120 to substantially prevent separation of the electrode and the reservoir while allowing the reservoir to be removed from the patient's skin. The application of ionizing radiation to cross-link the PVP has the added benefit of substantially eliminating any microorganisms present in the material so that if the material is subsequently handled under conditions that substantially prevent further introduction of microorganisms, the final packaged product is substantially free of microorganisms.

The preferred degree of cross-link is that which results in a swelling ratio of greater than 3. Additionally, because the bibulous material is constrained in the "x" and "y" directions by the reinforcement 116, best seen in FIG. 3, the swelling that occurs upon imbibement of aqueous solution during the charging of the reservoir-electrode with the medicament after crosslinking, preferably occurs substantially only in the "z" direction, i.e., to increase the distance between first surface 121 and second surface 123. Additionally, the degree of cross-link is preferably optimized so that the degree of swelling is controlled. If there is insufficient cross-linking, the swelling that occurs when the medicament is added may allow the formation of concentration imbalances about the electrodes thereby amplifying the corrosion process.

Most medicaments, including both the preferred medicaments, lidocaine and epinephrine are not stable to ionizing radiation, consequently in preparing the reservoir-electrode of the invention, medicaments generally cannot be incorporated into the aqueous poly(vinylpyrolidone) prior to the application of ionizing radiation for the cross-linking.

Since the cross-linked poly(vinylpyrolidone) is a hydrogel, the addition of any medicaments subsequent to the cross-linking is an elastic swelling process which is ultimately diffusion controlled that requires considerable time to reach equilibrium. Because of the recognition that the presence of chloride ion concentration gradients foster corrosion of the active electrode, a preselected amount of sodium chloride, which is unchanged by the ionizing radiation used for the cross-linking, is mixed with the poly(vinylpyrolidone) prior to the cross-linking ensuring a substantially uniform concentration of the chloride ion about electrode 112 or 114. The degree of cross-linking is preferably controlled to provide a preselected degree of adhesivity and cohesivity to the poly (vinylpyrolidone) hydrogel formed. When the preferred electron beam irradiation is used, preferably, the degree of crosslinking between one surface and another surface of the hydrogel is described by a gradient, so that a releasable adhesive bond may be formed between the surface applied to the patient's skin and an adhesive bond with a greater strength than the cohesive strength of the poly (vinylpyrolidone) hydrogel is formed between the electrode and the hydrogel.

Preferred iontophoretic device 100 is prepared by forming reservoir electrode into the crosslinked hydrogel as described above. Formed reservoir-electrode 104 that is intended to be the anode is then charged with the preferred aqueous lidocaine hydrochloride, epinephrine bitartrate and other excipients. Preferably, the lidocaine hydrochloride is present in an amount between about 50 mg to about 150 mg. Other amounts or other medicaments may be preferred for particular applications. In the prototype, about 100 mg of lidocaine hydrochloride is present. Epinephrine bitartrate is preferably present in an amount equivalent to about one-half to about one and one-half mg, and more preferably about one mg of the free base. Additionally, glycerin, sodium metabisulfite, editate disodium, citric acid, phenoxy ethanol, alkyl esters of hydroxybenzoic acid are included as humectants, antioxidants and antimicrobial preservatives in the preferred prototype active electrode 104. The prototype return electrode 108 has a preferred concentration of about 0.06 percent sodium chloride. Additionally, return electrode 108 may include excipients such as monobasic sodium phosphate, phenoxyethanol, alkyl esters of hydroxybenzoic acid, additional sodium chloride, glycerin and the like. For particular applications, other excipients are known, may be preferred and are considered within the scope of the invention.

Figure 4A:
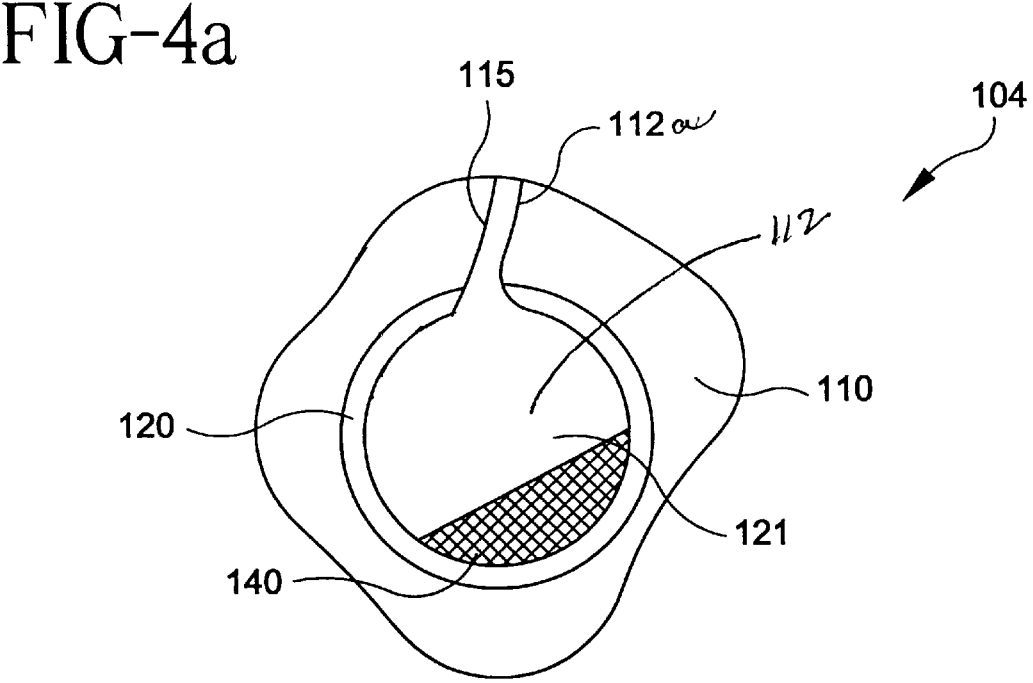
FIG. 4a is a schematic bottom plan view of a control sample of a reservoir-electrode similar to the reservoir-electrode of the invention after a period of shelf storage.
Figure 4B:
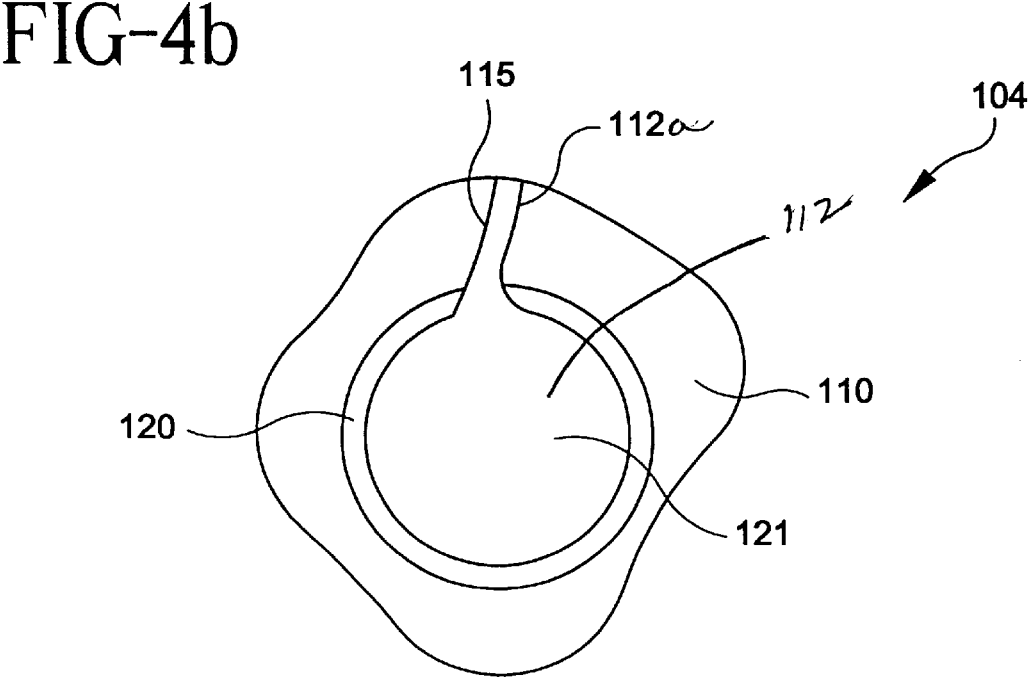

Referring to FIGS. 4a and 4b, schematic representations of photographs of reservoir-electrode 104 are shown. These schematic representations are indicative of the appearance of the reservoir-electrodes after storage for one year at 25° C. Samples (n=5) of both of the reservoir-electrodes in illustrated in FIGS. 4a and 4b were identically charged with aliquots of the preferred lidocaine hydrochloride, epinephrine bitartrate and excipients, sealed in a proposed final package and subjected to identical storage conditions (25° C., One year duration). In FIG. 4a a representation is shown of reservoir-electrode 104 prepared without the sodium chloride being mixed with the poly(vinylpyrolidone) prior to the cross-linking with ionizing radiation. The cross-hatched area 140 indicates a discolored area that developed during storage at ambient conditions. FIG. 4b is a schematic representation of reservoir-electrode 104 prepared with the preferred 0.06 percent sodium chloride (w/w) stored under identical conditions to the reservoir-electrode illustrated in FIG. 4b. The discolored area 140 seen in FIG. 4a is indicative of corrosion of the electrode material with the result that the cross-hatched portion of may be expected that a reservoir-electrode exhibiting the type of degradation schematically illustrated as 140 in FIG. 4a during storage may not deliver the expected amount of medicament to the patient.

In order for an iontophoretic system to be commercially viable and meet the necessary regulatory requirements, the reservoir-electrode must not substantially degrade during manufacture and shelf storage. The present invention, which substantially eliminates the corrosion of active electrodes caused by concentration gradients about the active electrode, allows a user to prepare for an iontophoretic delivery of a medicament by simply opening a package, applying the device to the skin and activating the power supply to initiate the preselected delivery of the medicament. The preferred iontophoretic reservoir-electrode and the complete iontophoretic device utilizing the reservoir-electrode of the invention are advances to the iontophoresis art and greatly improve the availability and efficiency of iontophoretic delivery of medicaments.

What is claimed is:

1. A method for preparing a reservoir-electrode assembly for an iontophoretic delivery device, comprising the step of adding an aliquot of a medicament solution including ions of an alkali metal halide salt to an electrode reservoir formed from an absorbent material having a substantially uniform concentration of the alkali metal halide salt therein.

2. The method of claim 1, wherein the alkaline metal halide salt is sodium chloride.

3. The method of claim 1, wherein the medicament solution comprises lidocaine HCl.

4. The method of claim 3, wherein medicament solution further comprises epinephrine.

5. The method of claim 1, wherein the absorbent electrode reservoir comprises from about 0.001% (w/w) to about 1% (w/w) sodium chloride.

6. The method of claim 1, wherein the absorbent electrode reservoir comprises about 0.06% (w/w) sodium chloride.

7. The method of claim 1, wherein the loading solution is applied to the reservoir as one or more droplets.

8. The method of claim 1, wherein the reservoir comprises a bibulous hydrophilic cross-linked material.

9. The method of claim 8, wherein the bibulous hydrophilic cross-linked material comprises poly (vinylpyrolidone).

10. The method of claim 1, wherein the electrode is a metal/metal halide electrode.

11. The method of claim 10, wherein the metal/metal halide electrode comprises silver and silver chloride.

12. The method of claim 1, wherein the medicament solution comprises a pharmacologically effective amount of lidocaine hydrochloride and epinephrine bitartrate.

13. A reservoir-electrode prepared according to a process for preparing the reservoir-electrode comprising the step of adding an aliquot of a medicament solution including ions of an alkali metal halide salt to an electrode reservoir formed from an absorbent material having a substantially uniform concentration of the alkali metal halide salt therein.

* * * * *

UNITED STATES PATENT AND TRADEMARK OFFICE
CERTIFICATE OF CORRECTION

PATENT NO.    : 6,629,968 B1
DATED         : October 7, 2003
INVENTOR(S)   : Jain et al.

It is certified that error appears in the above-identified patent and that said Letters Patent is hereby corrected as shown below:

Column 1,
Line 36, delete "products" and substitute therefor -- product's --.

Column 2,
Line 59, delete "surround" and substitute therefor -- surrounded --.
Line 60, delete "$C1_2$" and substitute therefor -- $C1_2$) --.

Column 4,
Line 36, delete "first-reservoir electrode" and substitute therefor -- first reservoir-electrode --.
Line 60, after "on the applied" delete "the".

Column 5,
Lien 36, after "answers" delete "the".

Column 6,
Line 14, delete "Preferred Device" and substiute therefor -- Preferred device --.
Line 29, after "mounted with" delete "a".
Line 41, delete "Inventors" and substitute therefor -- inventors --.

Column 7,
Line 5, delete "reservoir electrodes" and subsitute therefor -- reservoir-electrodes --.
Line 31, delete "Preferred 120" and substitute therefor -- Preferrred reservoir 120 --.

Column 8,
Line 8, delete "of about of about" and substitute therefor -- of about --.

Column 9,
Line 24, delete "reservoir electrodes" and subsitute therefor -- reservoir-electrodes --.
Line 52, after "reservoir-electrodes" delete -- in --.
Line 57, delete "One year" and substitute therefor -- one year --.

UNITED STATES PATENT AND TRADEMARK OFFICE
CERTIFICATE OF CORRECTION

PATENT NO.    : 6,629,968 B1
DATED         : October 7, 2003
INVENTOR(S)   : Jain et al.

It is certified that error appears in the above-identified patent and that said Letters Patent is hereby corrected as shown below:

Column 10,
Line 5, after "cross-hatched portion" delete -- of --.

Signed and Sealed this

Tenth Day of August, 2004

JON W. DUDAS
*Acting Director of the United States Patent and Trademark Office*